(12) United States Patent
Plail et al.

(10) Patent No.: US 8,101,170 B2
(45) Date of Patent: Jan. 24, 2012

(54) PROBIOTIC HEALTH OR FITNESS PROMOTING HUMAN OR ANIMAL FOODSTUFF AND/OR DRINKING WATER ADDITIVE AND USE THEREOF

(75) Inventors: Regina Plail, Langenlois (AT); Gerd Schatzmayr, Tulln (AT); Eva Maria Binder, Unterwart (AT); Michaela Mohnl, Tulln (AT); Alfred Klimitsch, Reidling (AT); Sabine Nitsch, St. Pölten (AT); Viviana Klose, Vienna (AT)

(73) Assignee: Erber Aktiengesellschaft, Herzogenburg (AT)

( * ) Notice: Subject to any disclaimer, the term of this patent is extended or adjusted under 35 U.S.C. 154(b) by 999 days.

(21) Appl. No.: 11/922,136

(22) PCT Filed: Jun. 14, 2006

(86) PCT No.: PCT/AT2006/000243
§ 371 (c)(1),
(2), (4) Date: Dec. 13, 2007

(87) PCT Pub. No.: WO2006/133472
PCT Pub. Date: Dec. 21, 2006

(65) Prior Publication Data
US 2010/0196323 A1     Aug. 5, 2010

(30) Foreign Application Priority Data

Jun. 14, 2005  (AT) .................................. A 999/2005

(51) Int. Cl.
| A23K 1/17 | (2006.01) |
| A23K 1/18 | (2006.01) |
| A23K 1/165 | (2006.01) |
| A61K 47/00 | (2006.01) |
| A61K 48/00 | (2006.01) |
| A01N 63/00 | (2006.01) |
| A01N 65/00 | (2009.01) |
| C12N 1/12 | (2006.01) |
| C12N 1/20 | (2006.01) |

(52) U.S. Cl. ..................... 424/93.3; 424/93.1; 424/93.4; 424/93.45; 424/438; 424/439; 424/442; 424/451; 435/252.1; 435/252.4; 435/252.9; 435/822; 435/853

(58) Field of Classification Search .................. None
See application file for complete search history.

(56) References Cited

U.S. PATENT DOCUMENTS

| 5,372,801 A | 12/1994 | Malmros et al. |
| 5,951,977 A | 9/1999 | Nisbet et al. |
| 2004/0115308 A1 | 6/2004 | Bengtsson-Riveros |

FOREIGN PATENT DOCUMENTS

| DE | 20202562 U1 | 6/2002 |
| EP | 1037964 | 9/2000 |
| WO | WO99/19459 | 4/1999 |
| WO | WO03/054168 | 7/2003 |
| WO | WO2004/032645 | 4/2004 |

*Primary Examiner* — Debbie K Ware
(74) *Attorney, Agent, or Firm* — Jacobson Holman PLLC (57) ABSTRACT

The invention relates to a probiotic health or fitness promoting human or animal foodstuff and/or drinking water additive, comprising a mixture of microorganisms, selected from the group *Enterococcus faecium*, DSM 16211, *Lactobacillus reuteri*, DSM 16350, *Lactobacillus salivarius* ssp. *salivarius*, DSM 16351, *Pediococcus acidilactici*, DSM 16210, *Bifidobacterium animalis* and DSM 16284. The invention further relates to a use of the human or animal foodstuff and/or drinking water additive, in particular for prevention of the harmful effect of a number of undesirable germs in the digestive system of animals and/or domestic birds.

25 Claims, 1 Drawing Sheet

FIGURE

PROBIOTIC HEALTH OR FITNESS PROMOTING HUMAN OR ANIMAL FOODSTUFF AND/OR DRINKING WATER ADDITIVE AND USE THEREOF

This is a national stage of International Application No. PCT/AT2006/000243 filed on Jun. 14, 2006 and published in German.

The present invention relates to a probiotic health and performance promoting food, feed and/or drinking water additive containing a mixture of microorganisms, and the use of such a probiotic health and performance promoting food, feed and/or drinking water additive.

Food, feed and/or drinking water additives containing mixtures of microorganisms are used to an increasing extent both in human and animal applications in order to prevent, as far as possible, infections by pathogenic germs such as, for instance, *Salmonella* or *E. coli, Campylobacter, Clostridia* etc. The use of such mixtures of microorganisms is based on what is called competitive exclusion (CE), by which it is attempted to suppress or eliminate "bad" bacteria, i.e. health-impairing or harmful bacteria, by so-called "good" bacteria. Thus, the growth of good bacteria inhibits that of bad bacteria, for instance by taking advantage from the environment of the digestive tract in terms of growth so as to proliferate more rapidly. Concretely, a special mixture of bacteria, which can also be isolated from the digestive tract, is used while trying to administer as broad a spectrum of intestinal bacteria as possible in order to achieve a wide field of application. However, the use of a spectrum as broad as possible, of intestinal bacteria which are not specified turned out to involve problems, since, on the one hand, possible problems of undefined mixtures such as, for instance, the transfer of antibiotic resistances or diseases can hardly be avoided and, on the other hand, the administration of undefined mixtures is limited by regional or international regulations and legislations in order to prevent unexpected or undesired results from the administration of such mixtures. The use of defined mixtures and, in particular, defined probiotic cultures comprising one or several strains will, therefore, have to be resorted to in order to avoid unexpected effects and to comply with the legislations.

Bearing in mind the legal provisions and seeking to obtain results as concrete as possible, a plurality of publications have recently become known, among which U.S. Pat. No. 5,372,810, for instance, describes a formulation and method for preventing and treating diarrhoea in farm animals by using sterilized bacterial cells, their homogenates or 'cell wall components, which were aerobically grown. The bacteria used in that case belong to the genera of *Brevibacterium* and/or *Corynebacterium*.

US Publication 2004-0115308 describes consumable products containing fresh, probiotic ingredients, said probiotics being comprised of the groups of yeasts, *Aspergilla, Lactobacilli, Bifidobacteria, Streptococci, Enterococci* and mixtures thereof. The bacteria used there are not dried or concentrated in any manner whatsoever, but are used as obtained, thus causing problems in terms of stability, applicability and the like.

From EP 1 037 964, a defined probiotic or formulation of anaerobic bacteria for controlling or inhibiting salmonellas in pigs has become known, said bacteria comprising *Enterococcus faecalis, Streptococcus bovis, Clostridium clostridiforme, Clostridium symbiosum, Clostridium ramosum, Bacteroides fragilis, Bacteroides distasonis, Bacteroides vulgatus, Bacteroides thetaiotamicron* and *Bacteroides caccae*, wherein at least seven different groups of germs have to be contained in the product.

Finally, WO 03/054168 describes a method for preparing a formulation of intestinal germs that are capable of eliminating pathogenic germs. In that method, a microbial sample is obtained from the intestines of a particular animal species and exposed to aerobic conditions, subsequently frozen, and rethawed. The individual microbial groups are selectively cultivated and tested for their activities against pathogenic microbes in inhibition tests and finally fermented and used.

The methods described in the literature, however, involve problems in that only one activity against a special pathogenic germ will be obtained by using either individual specific bacteria or combinations thereof. An activity against the various pathogenic germs contained in the digestive tract is not achievable. Finally, the methods described in the literature mostly also suffer from that the administered spectrum of bacteria is not broad enough to achieve as complete an inhibition of pathogenic germs as possible. Other known products use bacteria that are not obtained from the intestines, thus providing not completely specific activities.

The present invention aims to provide a probiotic health and performance promoting food, feed and/or drinking, water additive comprising a mixture of microorganisms, which displays its activity substantially in the entire digestive system of mammals and/or farm birds, thus preventing or at least reducing the harmful effects of a great number of undesired germs such as, e.g., *Salmonella, E. coli, Clostridia* etc.

To solve these objects, a probiotic health and performance promoting food, feed and/or drinking water additive containing a mixture of microorganisms is used according to the present invention, which comprises at least two microorganisms selected from the group consisting of *Enterococcus faecium*, DSM 16211, *Lactobacillus reuteri*, DSM 16350, and *Lactobacillus salivarius* ssp. *salivarius*, DSM 16351, *Pediococcus acidilactici*, DSM 16210, and *Bifidobacterium animalis*, DSM 16284. By using microorganisms from the group consisting of *Enterococcus faecium*, DSM 16211, *Lactobacillus reuteri*, DSM 16350, and *Lactobacillus salivarius* ssp. *salivarius*, DSM 16351, *Pediococcus acidilactici*, DSM 16210, and *Bifidobacterium animalis*, DSM 16284, it is feasible, due to said microorganisms originating from the most diverse regions of the digestive tract such as, for instance, the appendix, jejunum, ileum or goiter, to substantially cover the entire digestive tract and, in particular, the gastro-intestinal region so as to successfully prevent pathogenic germs from working in the entire digestive tract.

With the exception of DSM 16284, *Bifidobacterium animalis*, which is supposed to constitute a new species, the deposited microorganisms are new strains of already known species, since they generally show more than 99% correspondence with known strains.

The individual sequences of the deposited strains are as follows:

```
Pediococcus acidilactici, DSM 16210
CCTGGCTCAGGATGAACGCTGGCGGCGTGCCTAATACATGCAAGTCGAAC

GAACTTCCGTTAATTGATTATGACGTGCTTGCACTGAATGAGATTTTAAC

ACGAAGTGAGTGGCGGACGGGTGAGTAACACGTGGGTAACCTGCCCAGAA

GCAGGGGATAACACCTGGAAACAGATGCTAATACCGTATAACAGAGAAAA

CCGCCTGGTTTTCTTTTAAAAGATGGCTCTGCTATCACTTCTGGATGGAC

CCGCGGCGCATTAGCTAGTTGGTGAGGTAACGGCTCACCAAGGCGATGAT

GCGTAGCCGACCTGAGAGGGTAATCGGCCACATTGGGACTGAGACACGGC
```

-continued

CCAGACTCCTACGGGAGGCAGCAGTAGGGAATCTTCCACAATGGACGCAA

GTCTGATGGTGCACGCCGCGTGAGTGAAGAAGGGTTTCGGCTCGTAAAGC

TCTGTTGTTAAAGAAGAACGTGGGTGAGAGTAACTGTTCACCCAGTGACG

GTATTTAACCAGAAAGCCACGGCTAACTACGTGCCAGCAGCCGCGGTAAT

ACGTAGGTGGCAAGCGTTATCCGGATTTATTGGGCGTAAAGCGAGCGCAG

GCGGTCTTTTAAGTCTAATGTGAAAGCCTTCGGCTCAACCGAAGAAGTGC

ATTGGAAACTGGGAGACTTGAGTGCAGAAGAGGATAGTGGAACTCCATGT

GTAGCGGTGAAATGCGTAGATATATGGAAGAACACCAGTGGCGAAGGCGG

CTGTCTGGTCTGTAACTGACGCTGAGGCTCGAAAGCATGGGTAGCGAACA

GGATTAGATACCCTGGTAGTCCATGCCGTAAACGATGATTACTAAGTGTT

GGAGGGTTTCCGCCCTTCAGTGCTGCAGCTAACGCATTAAGTAATCCGCC

TGGGGAGTACGACCGCAAGGTTGAAACTCAAAAGAATTGACGGGGGCCCG

CACAAGCGGTGGAGCATGTGGTTTAATTCGAAGCTACGCGAAGAACCTTA

CCAGGTCTTGACATCTTCTGCCAACCTAAGAGATTAGGCGTTCCCTTCGG

GGACAGAATGACAGGTGGTGCATGGTTGTCGTCAGCTCGTGTCG

Sequencing primer: 341 forward, 530 reverse
Contig from 2 partial sequences: 341f530r
Sequence length: 1094 bases in total
Correspondence with known strain 99.6%

*Lactobacillus reuteri*, DSM 16350
GGATGAACGCCGGCGGTGTGCCTAATACATGCAAGTCGTACGCACTGGCC

CAACTGATTGATGGTGCTTGCACCTGATTGACGATGGATCACCAGTGAGT

GGCGGACGGGTGAGTAACACGTAGGTAACCTGCCCCGGAGCGGGGGATAA

CATTTGGAAACAGATGCTAATACCGCATAACAACAAAAGCCACATGGCTT

TTGTTTGAAAGATGGCTTTGGCTATCACTCTGGGATGGACCTGCGGTGCA

TTAGCTAGTTGGTAAGGTAACGGCTTACCAAGGCGATGATGCATAGCCGA

GTTGAGAGACTGATCGGCCACAATGGAACTGAGACACGGTCCATACTCCT

ACGGGAGGCAGCAGTAGGGAATCTTCCACAATGGGCGCAAGCCTGATGGA

GCACACCGCGTGAGTGAAGAAGGGTTTCGGCTCGTAAAGCTCTGTTGTTG

GAGAAGAACGTGCGTGAGAGTAACTGTTCAYGCAGTGACGGTATCCAACC

AGAAAGTCACGGCTAACTACGTGCCAGCAGCCGCGGTAATACGTAGGTGG

CAAGCGTTATCCGGATTTATTGGGCGTAAAGCGAGCGCAGGCGGTTGCTT

AGGTCTGATGTGAAAGCCTTCGGCTTAACCGAAGAAGTGCATCGGAAACC

GGGCGACTTGAGTGCAGAAGAGGACAGTGGAACTCCATGTGTAGCGGTGG

AATGCGTAGATATATGGAAGAACACCAGTGGCGAAGGCGGCTGTCTGGTC

TGCAACTGACGCTGAGGCTCGAAAGCATGGGTAGCGAACAGGATTAGATA

CCCTGGTAGTCCATGCCGTAAACGATGAGTGCTAGGGTGTTGGAGGGTTT

CCGCCCTTCAGTGCCGGAGCTAACGCATTAAGCACTCCGCCTGGGGAGTA

CGACCGCAAGGTTGAAACTCAAAGGAATTGACGGGGGCCCGCACAAGCGG

TGGAAGCATGTGGTTTAATTCGAAGCTACGCGAAGAACCTTACCAGGTCT

TGACATCTTCCGCTAACCTAGAGATAAGGCGTTCCCTTCGGGGACAAA

TGACAGGTGGTGCATGGTCGTCGTCAGCTCGTG

-continued

Sequencing primer: 341 forward, 530 reverse
Contig from 2 partial sequences: 341f530r
Sequence length: 1083 bases in total
Correspondence with known strain 99.7%

*Lactobacillus salivarius* ssp. *salivarius*, DSM 16351
ACGCTGGCGGCGTGCCTAATACATGCAAGTCGAACGAAACTTTCTTACAC

CGAATGCTTGCATTCACTCGTAAGAAGTTGAGTGGCGGACGGGTGAGTAA

CACGTGGGTAACCTGCCTAAAAGAAGGGGATAACACTTGGAAACAGGTGC

TAATACCGTATATCTNTAAGGATCGCATGATCCTNAGATGAAAGATGGTT

CTGCTATCGCTTNTAGATGGACCCGCGGCGTATTANCTAGTTGGTGGGGT

AACGGCNTACCAAGGNGATGATACGTAGCCGAACTGAGAGGNTGATCGGC

CACATTGGGACTGAGACACGGCCCAAACTCCTACGGGAGGCAGCAGTAGG

GAATCTTCCACAATGGACGCAAGTCTGATGGTGCCCGCCGCGAGAGTGAA

GAAGGTCTTCGGATCGTAAAACTCTGTTGTTAGAGAAGAACACGAGTGAG

AGTAACTGTTCATTCGATGACGGTATCTAACCAGCAAGTCACGGCTAACT

ACGTGCCAGCAGCCGCGGTAATACGTAGGTGGCAAGCGTTGTCCGGATTT

ATTGGGCGTAAAGGGAACGCAGGCGGTCTTTTAAGTCTGATGTGAAAGCC

TTCGGCTTAACCGGAGTAGTGCATTGGAAACTGGAAGACTTGAGTGCAGA

AGAGGAGAGTGGAACTCCATGTGTAGCGGTGAAATGCGTAGATATATGGA

AGAACACCAGTGGCGAAAGCGGCTCTCTGGTCTGTAACTGACGCTGAGGT

TCGAAAGCGTGGGTAGCAAACAGGATTAGATACCCTGGTAGTCCACGCCG

TAAACGATGAATGCTAGGTGTTGGAGGGTTTCCGCCCTTCAGTGCCGCAG

CTAACGCAATAAGCATTCCGCCTGGGGAGTACGACCGCAAGGTTGAAACT

CAAAGGAATTGACGGGGGCCCGCACAAGCGGTGGAGCATGTGGTTTAATT

CGAAGCAACGCGAAGAACCTTACCAGGTCTTGACATCCTTTGACCACCTA

AAAAATTAGGTTTCCCTTCGGGGACAAAGTGACAGGTGGTGCATGGCTGT

CGTCAGCTCGTGTCGT

Sequencing primer: 341 forward, 530 reverse
Contig from 2 partial sequences: 341f530r
Sequence length: 1066 bases in total
Correspondence with known strain 99.5%

*Enterococcus faecium*, DSM 16211
CCTGGCTCAGGACGAACGCTGGCGGCGTGCCTAATACATGCAAGTCGAAC

GCTTCTTTTTCCACCGGAGCTTGCTCCACCGGAAAAAGAGGAGTGGCGAA

CGGGTGAGTAACACGTGGGTAACCTGCCCATCAGAAGGGGATAACACTTG

GAAACAGGTGCTAATACCGTATAACAATCAAAACCGCATGGTTTTGATTT

GAAAGGCGCTTTCGGGTGTCGCTGATGGATGGACCCGCGGTGCATTAGCT

AGTTGGTGAGGTAACGGCTCACCAAGGCCACGATGCATAGCCGACCTGAG

AGGGTGATCGGCCACATTGGGACTGAGACACGGCCCAAACTCCTACGGGA

GGCAGCAGTAGGGAATCTTCGGCAATGGACGAAAGTCTGACCGAGCAACG

CCGCGTGAGTGAAGAAGGTTTTCGGATCGTAAAACTCTGTTGTTAGAGAA

GAACAAGGATGAGAGTAACTGTTCATCCCTTGACGGTATCTAACCAGAAA

GCCACGGCTAACTACGTGCCAGCAGCCGCGGTAATACGTAGGTGGCAAGC

GTTGTCCGGATTTATTGGGCGTAAAGCGAGCGCAGGCGGTTTCTTAAGTC

-continued
```
TGATGTGAAAGCCCCGGCTCAACCGGGGAGGGTCATTGGAAACTGGGAG

ACTTGAGTGCAGAAGAGGAGAGTGGAATTCCATGTGTAGCGGTGAAATGC

GTAGATATATGGAGGAACACCAGTGGCGAAGGCGGCTCTCTGGTCTGTAA

CTGACGCTGAGGCTCGAAAGCGTGGGGAGCAAACAGGATTAGATACCCTG

GTAGTCCACGCCGTAAACGATGAGTGCTAAGTGTTGGAGGGTTTCCGCCC

TTCAGTGCTGCAGCTAACGCATTAAGCACTCCGCCTGGGGAGTACGACCG

CAAGGTTGAAACTCAAAGGAATTGACGGGGCCCGCACAAGCGGTGGAGC

ATGTGGTTTAATTCGAAGCAACGCGAAGAACCTTACCAGGTCTTGACATC

CTTTGACCACTCTAGAGATAGAGCTTCCCCTTC

Sequencing primer: 341 forward, 530 reverse
Contig from 2 partial sequences: 341f530r
Sequence length: 1033 bases in total
Correspondence with known strain 99.9%

Bifidobacterium animalis, DSM 16284
TTGCCATGGGCGCAAGCCTGATGCAGCGACGCCGCGTGCGGGATGGAGGC

CTTCGGGTTGTAAACCGCTTTTGTTCAAGGGCAAGGCACGGTTTCGGGCC

GTGTTGAGTGGATTGTTCGAATAAGCACCGGCTAACTACGTGCCAGCAGC

CGCGGTAATACGTAGGGTGCGAGCGTTATCCGGATTTATTGGGCGTAAAG

GGCTCGTAGGCGGTTCGTCGCGTCCGGTGTGAAAGTCCATCGCCTAACGG

TGGATCTGCGCCGGGTACGGGCGGGCTGGAGTGCGNTAAGGGAGACTGGA

ATTCCCGGTGTAACGNTGGAATGTGTANATATCGGGAAGAACACCAATGG

NNAANGNAGGTCTCTGGGCCGTTACTGACGCTGACGATNNAAAGACGTGA

ACCAGCGANCNCNATAANATACCCTGACTACGGATTAGATACCCTGGTAG

TCCACGCCGTAAACGGTGGATGCTGGATGTGGGGCCCTTTCCACGGGTCC

TGTGTCGGAGCCAACGCGTTAAGCATCCCGCCTGGGGAGTACGGCCGCAA

GGCTAAAACTCAAAGAAATTGACGGGGCCCGCACAAGCGGCGGAGCATG

CGGATTAATTCGATGCAACGCGAAGAACCTTACCTGGGCTTGACATGTGC

CGGATCGCCGTGGAAACACGGTTTCCCTTCGGGGCCGGTTCACAGGTGGT

GCATGGTCGTCGTCAGCTCGTGTCGTGAGATGTTGGGTTAAGTCCCGCAA

CGAGCGCAACCCTCGCCGCATGTTGCCAGCGGGTGATGCCGGGAACTCAT

GTGGGACCGCCGGGGTCAACTCGGAGGAAGGTGGGGATGACGTCAGATCA

TCATGCCCCTTACGTCCAGGGCTTCACGCATGCTACAATGGCCGGTACAA

CGCGATGCGACACGGTGACGTGGGCGGATCGCTGAAAACCGGTCTCAGT

TCGGATCGCAGTCTGCAACTCGACTGCGTGAAGGCGGAGTCGCTAGTAAT

CGCGGATCAGCAACGCCGCGGTGAATGCGTTCCCGGGCCTTGTACACACC

GCCCGTCAAGTCATGAAAGTGGGTAGCACCGGAAGCCGGTGGCCCGACCC

TCGTGGGGCGGACCGTCTAATGGTGAGACTCGTGATTGG
```

```
Sequencing primer: 341 forward, 1492
reverse
Contig from 2 partial sequences: 341f1492r
Sequence length: 1139 bases in total
Correspondence with known strain 98.9% - new
species
```

According to a further development of the invention, the food, feed and/or drinking water additive comprises at least three microorganisms, thus enabling the achievement of a more complete coverage of the entire digestive tract and, in addition, the detection of a synergistic effect of the three used microorganisms against pathogenic germs.

A mixture comprising *Enterococcus faecium*, DSM 16211, *Lactobacillus reuteri*, DSM 16350, and *Lactobacillus salivarius* ssp. *salivarius*, DSM 16351, has turned out to be a particularly preferred mixture for food, feed and/or drinking water additives. Such a mixture not only has proved to be beneficial for the inhibition of pathogenic germs, in particular *E. coli* bacteria, but, on account of its strong pH-lowering potential and high acid production rates, e.g. of lactic acid, also strongly restricts the milieu for pathogenic germs, thus, in addition, also strongly inhibiting the settlement of other, different pathogens.

Furthermore, a food, feed and/or drinking water additive comprising *Enterococcus faecium*, DSM 16211, *Pediococcus acidilactici*, DSM 16210, and *Bifidobacterium animalis*, DSM 16284, is particularly preferred. Such a food, feed and/or drinking water additive, in particular, exhibits a uniformly enhanced inhibition of nearly all commonly present pathogenic germs and, in particular, *E. coli, Salmonella choleraesuis, Campylobacter jejuni, Clostridium perfringens*, which is increased relative to the single effects of the microorganisms contained in the mixture by such an extent as to provide a synergistic effect of the three microorganisms against a plurality of pathogenic germs. In addition, this mixture too has a strong pH-lowering potential, particularly on account of relatively high amounts of lactic acid and acetic acid forming, which will again have a strongly adverse effect on the living conditions for pathogenic germs.

Due to the fact that, as in correspondence with a preferred further development of the present invention, nutritive substances and/or prebiotic substances additionally usable as carriers and selected from fructo-oligosaccharides, inulins, isomalto-oligosaccharides, lactitol, lactosucrose, lactulose, pyrodextrines, soy oligosaccharides, transgalacto-oligosaccharides, xylo-oligosaccharides, vitamins, in particular vitamin E, are contained in the food, feed and/or drinking water additive, the living conditions for the used microorganisms in the digestive tract will be markedly improved, and it will, in particular, be safeguarded that the used microorganisms will be able to rapidly and reliably propagate in the digestive tract, yet while, at the same time, impeding or preventing the propagation of pathogenic germs by competitive exclusion. The used nutritive substances and/or prebiotic acids provide growth advantages for the used microorganisms relative to pathogenic germs.

Since, as in correspondence with a preferred further development of the present invention, a further carrier selected from zeolites, calcium carbonate, magnesium carbonate, trehalose, chitosan, shellac, albumin, starch, skim-milk powder, sweet-whey powder, maltodextrins, lactose, inulin, dextroses, vegetable oils, or a solvent selected from water or physiologic saline solution, is contained, it is feasible to obtain a uniform distribution of the microorganisms in the digestive tract, on the one hand, and to obtain further assistance of the competitive exclusion, on the other hand.

Since, as in correspondence with a preferred further development of the invention, a coating material selected from maltodextrins, guar seed flour, gum arabic, alginates, modified starch and starch derivates, dextrins, cellulose derivates like cellulose ester and ether, proteins like gelatine, albumin, casein, gluten, acacia gum, tragacanth, lipids like waxes, paraffin, stearic acid, mono- and diglycerides is contained, it is feasible to coat the microorganisms together with optionally contained carrier materials so as to ensure that the microorganisms will only develop their activities on the location of their purpose of use, i.e. in the digestive tract. Moreover, by using such coating materials, it is, for instance, possible to apply the food, feed and/or drinking water additive directly on animals to be treated therewith, such as day-old chicks, in their transport boxes by so-called gel or pellet application so as to provide a prophylaxis and therapeutic treatment of young animals against infections by pathogenic microbes. Such applications are of particular importance in modern animal breeding, since, because of the lacking direct contact of young animals with their mothers, the appropriate basis for an intact intestinal flora will no longer be passed on.

In order to achieve an even more complete activity of the food, feed and/or drinking water additive against pathogenic germs, the additive is preferably further developed to the effect that it additionally comprises at least one microorganism selected from the group of *Bifidobacterium* sp., *Lactobacillus salivarius*, *Lactobacillus* sp., *Lactobacillus fermentum* and *Enterococcus faecalis*. By admixing to the food, feed and/or drinking water additive a further microorganism known per se, the activity against one or several pathogenic germ(s) to be expected in the respective animals will be selectively enhanced so as to ensure further reduction of the risk of infection.

According to a preferred further development, it has turned out to be particularly beneficial to use the food, feed and/or drinking water additive in suspended, powdery or encapsulated form with a maximum diameter of 2000 μm so as to enable the exact, selective release of the activity of the microorganisms as a function of the desired location of use such as, for instance, the goiter, the stomach, the small intestine and the like. In addition, it is, of course, also possible to use mixed forms of suspended and encapsulated food, feed and/or drinking water additives, in order to be able to ensure an activity over the entire digestive system.

According to a preferred further development of the invention, a feed additive is provided, in particular for farm birds and/or pigs to increase the performance of said farm animals, which feed additive is comprised of $1\times10^7$ to $1\times10^{14}$, in particular $1\times10^{10}$ to $1\times10^{12}$, CFU/kg feed additive *Enterococcus faecium*, DSM 16211, and $1\times10^6$ to $1\times10^{14}$, in particular $1\times10^{10}$ to $1\times10^{12}$, CFU/kg feed additive *Lactobacillus reuteri*, DSM 16350. Such a selection of the amounts of used microorganisms, in particular, ensures the production of a feed additive displaying excellent activity against most of the *E. coli* germs.

According to a preferred further development of the invention, a feed additive is provided, in particular for farm birds and/or pigs to increase the performance of said farm animals, which feed additive is comprised of $1\times10^7$ to $1\times10^{14}$, in particular $1\times10^{10}$ to $1\times10^{12}$, CFU/kg feed additive *Enterococcus faecium*, DSM 16211, $1\times10^7$ to $1\times10^{14}$, in particular $1\times10^{10}$ to $1\times10^{12}$, CFU/kg feed additive *Pediococcus acidilactici*, DSM 16210, and $1\times10^7$ to $1\times10^{14}$, in particular $1\times10^{10}$ to $1\times10^{12}$, CFU/kg feed additive *Bifidobacterium animalis*, DSM 16284. Such a feed additive, in particular, ensures to strongly, or uniformly strongly, inhibit the action of *Salmonella choleraesuis* and *Clostridium perfringens* as well as the action of *E. coli* bacteria and, in addition, to strongly lower the pH in the digestive tract of the thus fed animals on account of the high production of acids, namely acetic acid and lactic acid, by the microorganisms used, thus strongly impeding further pathogenic germs from growing.

To increase the activity of the feed additive, it is preferably further developed to the effect that it is comprised of $1\times10^7$ to $1\times10^{14}$, in particular $1\times10^{10}$ to $1\times10^{12}$, CFU/kg feed additive *Enterococcus faecium*, DSM 16211, $1\times10^6$ to $1\times10^{14}$, in particular $1\times10^{10}$ to $1\times10^{12}$, CFU/kg feed additive *Lactobacillus reuteri*, DSM 16350, and $1\times10^6$ to $1\times10^{14}$, in particular $1\times10^{10}$ to $1\times10^{12}$, CFU/kg feed additive *Lactobacillus salivarius* ssp. *salivarius*, DSM 16351. Such a selection of the amounts of used microorganisms, in particular, ensures the production of a feed additive displaying excellent activity against *E. coli* germs and, in addition, on account of the high pH lowering potential, providing strong inhibition of the growth of nearly all other pathogenic germs.

The feed additive intended, in particular, for farm birds and/or pigs to increase the performance of said farm animals, according to a preferred further development of the present invention is comprised of $1\times10^7$ to $1\times10^{14}$, in particular $1\times10^{10}$ to $1\times10^{12}$, CFU/kg feed additive *Enterococcus faecium*, DSM 16211, $1\times10^6$ to $1\times10^{14}$, in particular $1\times10^{10}$ to $1\times10^{12}$, CFU/kg feed additive *Lactobacillus reuteri*, DSM 16350, $1\times10^6$ to $1\times10^{14}$, in particular $1\times10^{10}$ to $1\times10^{12}$, CFU/kg feed additive *Lactobacillus salivarius* ssp. *salivarius*, DSM 16351, $1\times10^7$ to $1\times10^{14}$, in particular $1\times10^{10}$ to $1\times10^{12}$, CFU/kg feed additive *Pediococcus acidilactici*, DSM 16210, $1\times10^7$ to $1\times10^{14}$, in particular $1\times10^{10}$ to $1\times10^{12}$, CFU/kg feed additive *Bifidobacterium animalis*, DSM 16284, and $1\times10^6$ to $1\times10^{14}$, in particular $1\times10^{10}$ to $1\times10^{12}$ CFU/kg, feed additive *Bifidobacterium* sp. 2. Such a feed additive mixture, in particular, shows a markedly increased activity against the pathogenic germs *Campylobacter jejuni* as well as *Salmonella choleraesuis*. Moreover, also the activities against common *E. coli* bacteria are strongly enhanced and, in the main, largely exceed the activities of the individual strains. In addition, the metabolic reaction of such a feed additive has proved that a synergistic effect of the bacteria must be present. Thus, the present mixture of five microorganisms, inter alia, is able to convert xylitol, which cannot be done by a microorganism of the mixture alone. The reason for this is that, for instance, several enzymes are required for the degradation of xylitol, and it is only by the combination according to the invention of five microorganisms that the necessary enzymes are made available jointly so as to enable the conversion of a carbon hydrate that is so complicated to degrade.

According to a preferred further development, the feed additive additionally comprises 1% and 95%, in particular 20% to 98%, of a carrier or natural substance. By a carrier or natural substance being additionally contained, a further elimination of pathogenic germs from the gastrointestinal environment is feasible by supporting or promoting the selective growth of the microorganisms used.

Since, as in correspondence with a preferred further development of the invention, the aqueous bacterial suspension is applied on the feed or its pellets in an amount of from 0.01 g/kg to 10 g/kg feed, in particular 0.025 g/kg to 2.5 g/kg feed, it is ensured that, on the one hand, the feed additive will be readily taken up by the animals and, on the other hand, pathogenic germs already present on the surface of the feed prior to the feed intake will be combated or eliminated or degraded by the feed additive. In order to achieve a particularly good activity of the feed additive, the feed additive is preferably mixed into the feed in an amount of from 20 g/t to 20 kg/t, in particular 100 g/t to 2.5 kg/t, thus providing a sufficient amount of microorganisms, on the one hand, and ensuring the safe degradation or elimination of pathogenic germs from the gastrointestinal environment, on the other hand.

According to a preferred further development of the invention, the microorganisms, or mixture of microorganisms, is used as a drinking water additive, wherein, according to a preferred further development, the drinking water additive comprises $1\times10^7$ to $1\times10^{14}$, in particular $1\times10^{10}$ to $1\times10^{13}$, CFU/kg drinking water additive *Enterococcus faecium*, DSM 16211, and $1\times10^6$ to $1\times10^{14}$, in particular $1\times10^{10}$ to $1\times10^{13}$, CFU/kg drinking water additive *Lactobacillus reuteri*, DSM 16350. Such a drinking water additive is, in particular, beneficial for the inhibition of pathogenic germs and, in particular, for the inhibition of *E. coli*. Moreover, such a mixture is able to strongly lower the pH in the gastrointestinal tract on account of the formation of lactic acid, acetic acid and propionic acid, thus creating unfavourable living conditions for pathogenic germs, and, on the other hand, the acids formed will also act bactericidally in their non-dissociated forms, as is generally known, so as to provide an altogether good action against a plurality of pathogenic germs.

According to a preferred further development, a drinking water additive is used, which is comprised of $1 \times 10^7$ to $1 \times 10^{14}$, in particular $1 \times 10^{10}$ to $1 \times 10^{13}$, CFU/kg drinking water additive *Enterococcus faecium*, DSM 16211, $1 \times 10^6$ to $1 \times 10^{14}$, in particular $1 \times 10^{10}$ to $1 \times 10^{13}$, CFU/kg drinking water additive *Lactobacillus reuteri*, DSM 16350, and $1 \times 10^6$ to $1 \times 10^{14}$, in particular $1 \times 10^{10}$ to $1 \times 10^{13}$, CFU/kg drinking water additive *Lactobacillus salivarius* ssp. *salivarius*, DSM 16351. Such a drinking water additive has turned out to be of particular benefit for the inhibition of *E. coli* as well as *Salmonella choleraesuis* and, in addition, also shows a synergistic effect in respect to the metabolic profile. This mixture is, thus, for instance, able to degrade D-tagatose, which cannot be done by any separate individual strain contained therein. A synergistic effect of these three strains in respect to the metabolic profile is, thus, detectable.

According to a preferred further development, the invention is further developed to the effect that the drinking water additive is comprised of $1 \times 10^7$ to $1 \times 10^{14}$, in particular $1 \times 10^{11}$ to $1 \times 10^{13}$, CFU/kg drinking water additive *Enterococcus faecium*, DSM 16211, $1 \times 10^7$ to $1 \times 10^{14}$, in particular $1 \times 10^{10}$ to $1 \times 10^{13}$, CFU/kg drinking water additive *Pediococcus acidilactici*, DSM 16210, and $1 \times 10^7$ to $1 \times 10^{14}$, in particular $1 \times 10^{10}$ to $1 \times 10^{13}$, CFU/kg drinking water additive *Bifidobacterium animalis*, DSM 16284. Such a mixture of microorganisms has turned out to be of particular benefit for the inhibition of pathogenic germs of the group of *Salmonella choleraesuis, Campylobacter jejuni* and *Clostridium perfringens* and, due to the different origins of the microorganisms from the gastrointestinal tract, is, moreover, also able to develop its activity over the entire gastrointestinal tract so as to ensure an almost complete elimination of harmful, pathogenic germs from the entire gastrointestinal system.

According to a preferred further development, a drinking water additive is used, which is comprised of $1 \times 10^7$ to $1 \times 10^{14}$, in particular $1 \times 10^{10}$ to $1 \times 10^{13}$, CFU/kg drinking water additive *Enterococcus faecium*, DSM 16211, $1 \times 10^6$ to $1 \times 10^{14}$, in particular $1 \times 10^{10}$ to $1 \times 10^{13}$, CFU/kg drinking water additive *Lactobacillus reuteri*, DSM 16350, $1 \times 10^6$ to $1 \times 10^{14}$, in particular $1 \times 10^{10}$ to $1 \times 10^{13}$, CFU/kg drinking water additive *Lactobacillus salivarius* ssp. *salivarius*, DSM 16351, $1 \times 10^7$ to $1 \times 10^{14}$, in particular $1 \times 10^{10}$ to $1 \times 10^{13}$, CFU/kg drinking water additive *Pediococcus acidilactici*, DSM 16210, $1 \times 10^7$ to $1 \times 10^{14}$, in particular $1 \times 10^{10}$ to $1 \times 10^{13}$, CFU/kg drinking water additive *Bifidobacterium animalis*, DSM 16284, and $1 \times 10^6$ to $1 \times 10^{14}$, in particular $1 \times 10^{10}$ to $1 \times 10^{13}$ CFU/kg drinking water additive *Bifidobacterium* sp. By such a drinking water additive, it is feasible to inhibit almost all frequently occurring pathogenic germs and, in particular, *E. coli, Salmonella, Clostridia* and *Campylobacter* to a degree largely exceeding that of the cumulative action of the individual microorganisms, so that a massive synergistic effect against pathogenic germs will be achieved. In addition, it is feasible by such a microorganism to strongly and extremely rapidly lower the pH in the digestive tracts of animals so as to further enhance its action and, in particular, the inhibition of the growth of pathogenic germs.

In order to promote, in particular, the growth of the desired microorganisms in the gastrointestinal tract and further enhance the elimination effect, the drinking water additive according to a preferred further development additionally comprises 1% to 95%, in particular 20% to 92%, of a carrier or nutrient.

According to a further object, the present invention aims to selectively boost the immune systems of mammals and/or farm birds by the selective use of microorganisms, or a mixture of microorganisms, and thereby eliminate as completely as possible pathogenic germs from the digestive tract.

To solve these objects, the invention contemplates the use of a mixture of at least two microorganisms selected from the group consisting of *Enterococcus faecium*, DSM 16211, *Lactobacillus reuteri*, DSM 16350, and *Lactobacillus salivarius* ssp. *salivarius*, DSM 16351, *Pediococcus acidilactici*, DSM 16210, and *Bifidobacterium animalis*, DSM 16284, as a probiotic health and performance promoting food, feed and/or drinking water additive. Such a use enables to almost completely eliminate pathogenic germs from the digestive tracts of mammals and farm animals by the so-called competitive exclusion, since an extremely rapid and strong lowering of the pH in the digestive tract is, in particular, feasible by a selective mixture of said microorganisms, the use according to the invention enabling the selective inhibition of the development of pathogenic germs. Apart from that, none of the microorganisms exhibited an antibiotic resistance even at an extended, simultaneous administration of at least one antibiotic during such use.

According to a preferred further development, a mixture of *Enterococcus faecium*, DSM 16211, *Lactobacillus reuteri*, DSM 16350, and *Lactobacillus salivarius* ssp. *salivarius*, DSM 16351, is used according to the present invention. Such a use, in particular, ensures the inhibition of the action of pathogenic germs, namely *E. coli*, and, by the extremely rapid lowering of the pH in the digestive tract, to deteriorate the living conditions for pathogenic germs as such to such a degree that even the growth of any other harmful germs will be strongly impaired or inhibited so as to markedly reduce the susceptibility to diseases of mammals and/or farm birds supplied therewith.

According to a further development of the invention, a mixture of *Enterococcus faecium*, DSM 16211, *Pediococcus acidilactici*, DSM 16210, and *Bifidobacterium animalis*, DSM 16284, is preferably used, which, in particular, renders feasible the inhibition of *Salmonella choleraesuis, Campylobacter jejuni* and *Chlostridium perfringens,* respectively, and, in addition, strongly deteriorates the living conditions for other pathogenic germs, so that, in the main, a probiotic effect of the used mixture largely. exceeding the cumulative' effect when using the individual microorganisms can be demonstrated.

According to a preferred further development of the invention, a mixture comprised of *Enterococcus faecium*, DSM 16211, *Lactobacillus reuteri*, DSM 16350, is used along with other strains from these groups of *Lactobacilli, Streptococci* and/or *Bifidobacteria*, the additional use of strains from these groups of *Lactobacilli, Streptococci* and/or *Bifidobacteria* allowing the selective use or selective inhibition of special microorganisms in selective regions of the gastrointestinal tract so as to particularly inhibit the occurrence of a specific disease caused by pathogenic germs.

According to a preferred further development of the invention, the mixture of microorganisms is used to strengthen the immune defence. Such a use is, in particular, enabled by the selective choice of the microorganisms used and their origins from the most diverse regions of the digestive tract safeguarding that the microorganisms used will develop their activities over the entire length of the digestive system and, hence, will, in fact, markedly strengthen the immune defence of the thus treated mammal or farm bird against specific pathogenic germs in the entire digestive tract.

According to a preferred further development, the mixture of microorganisms is used along with at least one gelatinizing agent and/or pellet former or coating material selected from maltodextrins, guar seed flour, gum arabic, alginates, modified starch and starch derivates, dextrins, cellulose derivates, proteins, acacia gum, tragacanth, lipids. By using the mixture of microorganisms together with a gel and/or pellet former, its use as a so-called pellet of gel application becomes feasible so as to allow, in particular, extremely young animals which can no longer be supplied with the appropriate immunoenhancing substances by their mothers to be safely and reliably supplied with the necessary microorganisms required to strengthen their immune defence. When using such a gel or pellet application, the mixture of microorganisms is covered with gelatinizing agents or encapsulated, and this mixture is directly sprayed or applied on the young animals to be supplied therewith, or, for instance, introduced into transport boxes in the event of young chicks, so as to safeguard the supply of the young animals with the microorganisms that are of essential importance to them. A similar, preferred use will be accomplished in that the mixture of microorganisms, along with a liquid carrier, as a spray suspension is directly applied on the young animals to be treated therewith. By spraying young animals with the mixture of microorganisms, a portion of this spray mixture will be taken up into the digestive tract by their own coat care or contact with other young animals, whereby the supply with the microorganisms that are essential for strengthening their immune defence will again be safeguarded.

BRIEF DESCRIPTION OF THE DRAWINGS

FIG. 1 describes composition of intestinal microflora., to produce said additive comprising the mixture of microorganisms In the following, the invention will be explained in more detail by way of exemplary embodiments. Therein, Example 1 illustrates the inhibition of pathogenic germs by isolated test germs in an agar plate assay model; Example 2 illustrates a feeding test in which day-old chicks are fed a feed and drinking water additive containing five, three or no microorganisms; Example 3 is a field study in which day-old chicks are fed a drinking water additive containing five microorganisms; Example 4 illustrates a feeding test in which day-old chicks received a drinking water additive containing five microorganisms at defined times; Example 5 demonstrates *Salmonella* challenge in day-old chicks which were administered microorganisms either through drinking water or through fodder at defined times, with a mixture of three or five microorganisms having been used; and Example 6 shows a feeding test in weaned piglets.

EXAMPLE 1

Inhibition of Pathogenic Germs by the Isolated CE TEST Germs (Competitive Exclusion Test Germs) According to the Invention in an Agar Plate Assay Model The assay was performed on MRS agar plates. The strains were applied on the agar plates by inoculation, the strains having been directly taken from cooling vials. The incubation of the plates took place for 48 hrs under anaerobic conditions. After the culturing of the pathogenic strains in the appropriate media, the plates were carefully poured with about 9 ml of semisolid medium containing the respective pathogenic strain. For *E. coli* and *Salmonella chloeraesuis*, semisolid VL medium, for *Campylobacter jejuni*, semisolid Brain Heart Infusion Medium, and for *Clostridium perfringens*, semisolid *Reinforced Clostridial* Medium, were used.

The plates were subsequently incubated under the respective incubation conditions of the pathogenic strains. The evaluation of the plates was effected by measuring the diameters of the test germs and inhibition zones and calculating therefrom the inhibition zone to test germ ratios. Based on the inhibition zone/test germ ratios, an assessment of the inhibiting action of the test germs can be made. Table 1 below indicates the results for the strains used separately and in mixture.

TABLE 1

| Isolate | Strain | *E. coli* | *E. coli* | *Salmonella choleraesuis* | *Campylobacter jejuni* | *Clostridium perfringens* |
|---|---|---|---|---|---|---|
| DSM 16211 | *Enterococcus faecium* | 2.11 | 1.44 | 1.37 | 1.28 | 1.43 |
| DSM 16284 | *Bifidobacterium animalis* | 0.45 | 0.85 | 0.84 | 0.33 | 1.85 |
| DSM 16210 | *Pediococcus acidilactici* | 1.52 | 1.38 | 1.34 | 1.47 | 1.51 |
| DSM 16351 | *Lactobacillus salivarius* | 1.49 | 2.26 | 1.46 | 1.50 | 2.05 |
| DSM 16350 | *Lactobacillus reuteri* | 2.53 | 1.42 | 1.60 | 1.36 | 2.12 |
| area | | 0.45-2.5 | 0.85-2.26 | 0.84-1.37 | 0.33-1.5 | 1.01-2.12 |
| NCIMB 10415 | *Enterococcus faecium* | 1.37 | 1.35 | 1.20 | 1.22 | 1.31 |
| DSM 20104 | *Bifidobacterium animalis* | 0.41 | 0.79 | 0.65 | 0.31 | 1.42 |
| DSM 20284 | *Pediococcus acidilactici* | 1.41 | 1.20 | 1.10 | 1.32 | 1.35 |
| DSM 20555 | *Lactobacillus salivarius* | 1.40 | 2.19 | 1.09 | 1.41 | 1.63 |
| DSM 20016 | *Lactobacillus reuteri* | 2.14 | 1.30 | 1.20 | 1.35 | 1.54 |
| Mean activity of individual strains | | 1.48 | 1.56 | 1.11 | 0.92 | 1.57 |

TABLE 1-continued

| Isolate | Strain | E. coli | E. coli | Salmonella choleraesuis | Campylobacter jejuni | Clostridium perfringens |
|---|---|---|---|---|---|---|
| DSM 16211, DSM 16210, DSM 16284 | | 1.70 | 1.70 | 1.90 | 1.30 | 1.60 |
| DSM 16211, DSM 16350, DSM 16351 | | 2.50 | 1.80 | 1.60 | 1.30 | 1.80 |
| DSM 16210, DSM 16211, DSM 16350, DSM 16351, DSM 16284 | | 2.60 | 1.90 | 2.10 | 1.70 | 1.90 |

From a comparison of the deposited microorganisms (written in bold letters) with related strains (written in cursive letters), it is clearly apparent that the deposited microorganisms (written in bold letters) are able to inhibit pathogenic germs at considerably higher degrees than already known strains (cursively written).

EXAMPLE 2

Feeding test in day-old chicks which were administered either a mixture of all five deposited microorganisms or a mixture of three deposited microorganisms, the mixtures having been administered via drinking water in the starting period and, additionally, via the feed during the whole test period.
Test Parameters:
600 day-old chicks (race: Ross 308) were divided into three groups:
Group 1: control without additives
Group 2: five microorganisms; days 1-21 in drinking water; days 1-42 via feed
Group 3: DSM 16210, DSM 16211, DSM 16284; day 1-21 in drinking water; days 1-42 via feed
Water and feed were available ad libitum for intake by the animals.
Recorded Performance Parameters:
Live weight, daily weight gains, feed intake, feed conversion ratio (=FCR), mortality, European Production Efficiency Factor (EPEF).

TABLE 2

Summary of performance data in feeding test

| Group | Live weight (g) | Daily gain (g) | Feed intake (g/animal) | FCR | Mortality | EPEF |
|---|---|---|---|---|---|---|
| Control | 2588$^a$ | 60.0 | 91.0 | 1.68 | 6.4 | 343 |
| DSM 16210, DSM 16211, DSM 16284 | 2657$^{ab}$ | 62.4 | 91.3 | 1.68 | 5.0 | 357 |
| DSM 16211, DSM 16284, DSM 16210, DSM 16351, DSM 16350 | 2689$^b$ | 63.1 | 92.3 | 1.69 | 3.3 | 366 |

$^{a,b}$sign. difference (P < 0.05)
*EPEF (European Production Efficiency Factor)

The use of the products allowed significant improvements in the live weights of the animals in the test groups. The feed intake could be slightly increased in the product group containing all five microorganisms, no difference was, however, observed in respect to the feed conversion ratio. The mortality was high in general, since the test was performed in midsummer and the animals were confronted with very high ambient temperatures. Despite this additional stress factor, a marked increase in the performance of the product groups could, however, be observed.

EXAMPLE 3

In a field test, a mixture of all five microorganisms was tested in day-old chicks under practical conditions and administered in drinking water over the entire period.
Test Parameters:
About 53,000 day-old chicks were equally divided between two storeys.
Ground floor: control without additives
1$^{st}$ floor: all five microorganisms in drinking water Water and feed were available ad libitum to the animals.
Recorded Performance Parameters:
Live weight, mortality
As is apparent from Table 3 below, the performances of the animals could be markedly increased, above all also in comparison to preceding production cycles listed in Table 4, with the previously occurring *E. coli* problems having been resolved.

TABLE 3

Summary of performance data

| | Live weight (g) | Mortality % |
|---|---|---|
| Ground floor | 2282 | 3.38 |
| 1st floor | 2328 | 3.03 |

TABLE 4

Performances of the farm's last six production cycles

| | Number of animals | Mortality (%) | Live weight (g) |
|---|---|---|---|
| 1 | 51000 | 5.55 | 2109 |
| 2 | 49990 | 6.46 | 2228 |
| 3 | 49000 | 2.65 | 2043 |
| 4 | 50592 | 5.41 | 1627 |
| 5 | 48450 | 5.09 | 1785 |
| 6* | 53244 | 3.20 | 2305 |

*with all five microorganisms

EXAMPLE 4

In a feeding test, day-old chicks were administered a mixture of all five microorganisms via drinking water at defined times.
Test Parameters:
400 day-old chicks, race: Ross 308, were divided between two groups according to the principle of contingency:
Group 1: control; without additives
Group 2: five microorganisms in drinking water on days 1, 2, 3, 7, 8, 9 and 14, 15, 16
Water and feed were available ad libitum for intake by the animals.
Recorded Performance Parameters:
Live weight gains, feed intake, feed conversion ratio (=FCR), mortality, EPEF (European Production Efficiency Factor).
The results are summarized in Table 5.

TABLE 5

Summary of performance data

|  | Control | Five microorganisms |
|---|---|---|
| Live weight (g) | 2320.66a | 2392.19b |
| Weight gain (g) | 54.17 | 55.87 |
| Feed consumption (g) | 4365 | 4482 |
| Feed conversion ratio (=FCR) | 1.92 | 1.90 |
| Mortality (%) | 1 | 1.5 |
| EPEF* | 285 | 295 | a, bsign. differences (P < 0.05)
*EPEF (European Production Efficiency Factor)

Due to the addition of the microorganisms, the live weights of the animals could be significantly increased. In terms of feed intake and feed conversion ratio, the two groups were comparable with each other. The productivity mass number (=EPEF) was clearly higher in the product group than in the control group.

EXAMPLE 5

*Salmonella* Challenge in Day-old Chicks
A product comprised of all five microorganisms, and a product comprised of three microorganisms, were administered in feed over the entire test period and via drinking water in the starting phase.
Test Parameters:
304 day-old chicks, race: Ross 308, were divided among four groups:
Group 1: negative control; without additives and without *Salmonella* challenge
Group 2: positive control; without additives; with *Salmonella* challenge
Group 3: with *Salmonella* challenge+product of five microorganisms: days 1-21 in drinking water; days 1-42 via feed
Group 4: with *Salmonella* challenge+product of three microorganisms (DSM 16211, DSM 16210, DSM 16284): days 1-21 in drinking water; days 1-42 via feed
Water and feed were available ad libitum for intake by the animals.
On day 5, all animals of groups 2, 3 and 4 were orally inoculated with a dose of 6×10⁵ cfu *Salmonella enteritidis*. The negative control was carried along for the control of the normal performance data.

Recorded Performance Parameters:
Live weight gain, feed intake, feed conversion ratio (=FCR), morbidity (measured by the number of diarrhoeas), mortality, EPEF (European Production Efficiency Factor).
The results are summarized in Table 6.

TABLE 6

Summary of performance data

|  | 1 | 2 | 3 | 4 |
|---|---|---|---|---|
| Total weight gain (g) | 2847.29$^a$ | 2632.39$^b$ | 2716.49$^{ab}$ | 2702.18 |
| Feed consumption (g) | 4790.07$^a$ | 4559.11$^b$ | 4534.30$^b$ | 4527.02 |
| Feed conversion ratio (=FCR) | 1.68 | 1.73 | 1.67 | 1.67 |
| % Morbidity | 6.34$^a$ | 19.14$^b$ | 15.65$^b$ | 16.79$^b$ |
| % Mortality | 0.96 | 0.47 | 0.72 | 0.669 |
| EPEF* | 422 | 385 | 416 | 412 |

$^{a,b}$sign. differences (P < 0.05)
*EPEF (European Production Efficiency Factor)

In regard to the total weight gain, notable performance losses occurred due to the infection with *Salmonella enteritidis* as compared to the control group, which could be improved by the addition of the products according to the invention. It was shown that marked improvements could be reached by the addition of both the product comprising three microorganisms and that comprising five micro-organisms. Also the feed intake had been adversely affected by the infection, yet the feed conversion ratio could be markedly improved by the addition of the products according to the invention. Even the morbidity, measured by the number of diarrhoeas observed, could be markedly reduced by the addition of the products as compared to the untreated group.

EXAMPLE 6

Feeding Test in Day-old Chicks—*Salmonella* challenge
Three groups each consisting of 36 day-old chicks were subjected to a feeding test using *Salmonella* challenge. A first group was administered none of the products, a second group was administered a mixture of all five deposited strains, and a third group received a commercially available probiotic product comprising the following microorganisms: *Lactobacillus* sp., *Lactobacillus* sp., *Bifidobacterium* sp and *Enterococcus faecium*.
Test Approach:
The day-old chicks were kept in cages in an isolated room. The probiotic products were administered on life days 1, 2 and 3 via the drinking water, which was supplied ad libitum to the chicks. On the third day of life, all chicks were orally administered 1.0 ml of a suspension of *Salmonella enteritidis*. The concentration of the *salmonella* solution was 1.0×10⁶ CFU/ml. All chicks additionally received feed and water ad libitum. The concentration of *salmonellas* in the animals' excrements was measured.
Evaluation:

| Group | Concentration of salmonellas in excrements (CFU log 10) |
|---|---|
| Commercially available probiotic product | 2.43$^b$ |
| Product mixture | n.d. (<2.00)$^a$ |
| Control | 3.2 |

The results demonstrate that only the combination of the five deposited microorganisms was able to significantly reduce the growth of salmonellas to such an extent that the number of *salmonella* germs fell below the detection limit.

EXAMPLE 7

Feeding test in weaned piglets, using a mixture comprising five microorganisms and a mixture comprising three microorganisms, respectively.

In a feeding test, the microorganisms according to the present invention were tested for their effects on the performances of weaned piglets. The products were administered via the feed over the entire test period of 47 days.

Test Parameters:

101 weaned piglets, race: ÖHYB, were divided among three groups:

Group 1: control without additives
Group 2: five microorganisms (C5); days 1-47 via feed;
Group 3: three microorganisms (C3) comprising DSM 16211, DSM 16350, DSM 16351; days 1-47 via feed Water and feed were available ad libitum for intake by the animals.

Recorded Performance Parameters:

Live weight, daily weight gains, feed intake, feed conversion ratio (=FCR), mortality The results are summarized in Table 7.

TABLE 7

Summary of performance data

|  | Control | C5 | Difference between C5 and control | C3 | Difference between C3 and control |
|---|---|---|---|---|---|
| Number of animals | 34 | 33 |  | 33 |  |
| Initial weight (kg) | 7.75 | 7.76 |  | 7.75 |  |
| Weight day 13 (kg) | 11.89 | 12.26 | +3.1% | 12.09 | +1.7% |
| Final weight (kg) | 31.67 | 33.00 | +4.2% | 32.5 | +2.6% |
| Daily gain days 1-13 (g) | 321 | 350 | +9.0% | 334 | +4.0% |
| Daily gain days 14-47 (g) | 582 | 610 | +4.8% | 600 | +3.09% |
| Daily gain days 1-47 (g) | 509 | 537 | +5.5% | 527 | +3.5% |
| Mortality (number) | 2 | 2 |  |  |  |

The use of the products allowed significant improvements in the live weights of the animals in the test groups, namely by 3% and 1.7%, respectively, after the first 13 days, and by 4% and 2.6%, respectively, until the end of the test. A marked increase by the addition of the products could also be obtained in terms of daily weight gains.

In Table 8 below, the feed data are summarized.

TABLE 8

Summary of feed data

|  | Control | C5 | Difference | C3 | Difference |
|---|---|---|---|---|---|
| Feed consumption (g) | | | | | |
| Days 1-13 | 495 | 511 | +3.2% | 504 | +1.8 |
| Days 14-47 | 1155 | 1193 | +3.3% | 1180 | +2.2 |
| Days 1-47 | 972 | 1033 | +6.3 | 1012 | +4.1 |

TABLE 8-continued

Summary of feed data

|  | Control | C5 | Difference | C3 | Difference |
|---|---|---|---|---|---|
| FCR (kg/kg) | | | | | |
| Days 1-13 | 1.76 | 1.66 |  | 1.68 |  |
| Days 14-47 | 1.98 | 2.02 |  | 2.00 |  |
| Days 1-47 | 1.95 | 1.96 |  | 1.95 |  |

The feed intakes could be slightly increased in the product groups, in terms of feed conversion ratios an improvement was above all noticed in the first test period. In the further course, no differences in the feed conversion ratios could, however, be determined.

List pursuant to Rule 13bis, para 4, of the Regulations Under the Patent Cooperation Treaty.

All of the microorganisms mentioned in the present application were deposited at the German Collection of Microorganisms and Cell Cultures GmbH—DSMZ, Mascheroder Weg 1b, 38124 Braunschweig, Germany (DE).

| Accession number | Accession date |
|---|---|
| DSM 16284 | Mar. 10, 2004 |
| DSM 16211 | Feb. 06, 2004 |
| DSM 16210 | Feb. 06, 2004 |
| DSM 16350 | Apr. 15, 2004 |
| DSM 16351 | Apr. 15, 2004 |

EXAMPLE 8

Positive Shift of Intestinal Flora in Broiler Chickens

Four groups of broiler chickens were subjected to a feeding test, 2 groups having been administered a product mixture comprised of five deposited microorganisms, one group having been a negative control without any additive, one group having been a positive control with the addition of an antibiotic performance promoter, namely avialmycin, one group having received the mixture of five microorganisms via drinking water, and one group having been administered the mixture of microorganisms via the feed.

In the course of examination, it turned out that there were no statistically significant differences among the individual groups in terms of the total count of aerobic germs, coliformes, the total count of anaerobic germs and bacteroids. The groups that had received the mixture of five microorganisms showed significantly higher germ numbers in respect to *Bifidobacterium* sp, *Lactobacillus* spp and Gram+cocci (e.g. *Enterococcus, Pediococcus*) when compared to the positive and negative controls (NK, PK).

Figure 1:
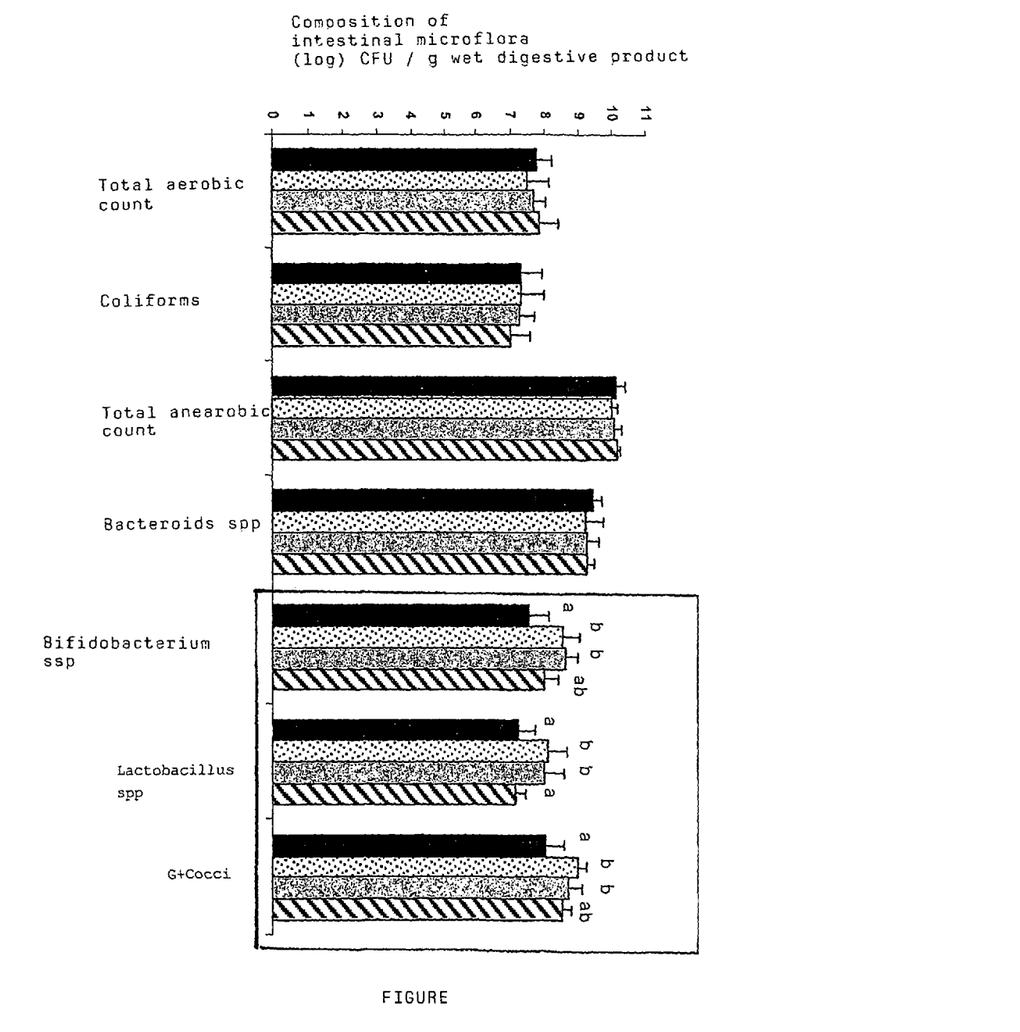

A flow chart of this comparison is illustrated in the Figure.

The flow chart of the Figure, in the black-framed part, shows that the groups having received the mixture of five microorganisms via drinking water or feed, respectively, exhibits considerably higher numbers of "good" germs. In the diagram of the Figure, the negative control group is represented as a black bar, the positive control group is represented as a hatched bar, the group that was administered the five microorganisms via the feed is indicated by a dotted bar, and the group that was administered the mixture of five microorganisms via the drinking water is illustrated as a plain grey bar.

EXAMPLE 9

Feeding Test in Broiler Chickens 4,500 broiler chickens (Ross 308) of mixed sexes were divided between two groups, each of the two groups having been subdivided into three further subgroups to facilitate observation. Both groups received a standard feedstuff, and the test group received a mixture of the five deposited microorganisms at a dose of $1*10^9$ CFU/kg feed. The control group was administered a commercially available probiotic product at the same dose. The administration of the substances was effected via the feedstuff.

After 38 days, it was found that the performance parameters of the test group were markedly improved both in terms of live weight and daily weight gains and feed conversion ratios. In addition, the mortality had significantly dropped relative to the comparative group. The results are indicated in Table 9 below.

TABLE 9

Results after 38 days

|  | Commercially available probitic product | C5 product mixture |
|---|---|---|
| Number of animals | 2250 | 2250 |
| Live weight (g) | 1875 | 2034 |
| Daily weight gains (g) | 52 | 56.5 |
| Feed conversion ratio | 1.66 | 1.61 |
| Mortality (%) | 1.15 | 0.40 |

EXAMPLE 10

In a laboratory test, the antibiotic resistances of the five deposited microorganisms were investigated and, where available, compared with the antibiograms of related bifidobacteria. It was only with the *Bifidobakterium animalis* strain that no comparative strain could be found in the literature or secured data could be obtained for comparative strains on account of difficult cultivation conditions. The results of the resistance tests in respect to common antibiotics, along with comparative strains where available, are indicated in the Tables below.

|  | *Pediococcus acidilacti*, DSM 16210 | *Pediococcus acidilacti*, reference strain |
|---|---|---|
| β-Lactams - ampicillin | S | S |
| Aminoglycodsides |  |  |
| Streptomycin | S | R |
| Kanamycin | S | R |
| Neomycin | S | R |
| Gentamicin | S | R |
| Amphenicol - chloroamphenicol | S | S |
| Macrolid - erythromycin | S | S |
| Ansamycin - rifampin | S | S |
| Streptogramin - chinu/dalfopristin | S | R |
| Fluorochinolone - enrofloxacin | S | n.a. |
| Oxazolidinone - linezolid | S | R |

|  | *Enterococcus faecium*, DSM 16211 | *Enterococcus faecium*, reference strain 1 | *Enterococcus faecium*, reference strain 2 |
|---|---|---|---|
| β-Lactame - ampicillin | S | S | S |
| Aminoglycosides |  |  |  |
| Streptomycin | S | R | S |
| Kanamycin | S | R | R |
| Neomycin | S | R | R |
| Gentamicin | S | R | S |
| Amphenicol - chloroamphenicol | S | S | S |
| Tetracyclin | S | R | S |
| Macrolide - erythromycin | S | R | R |
| Ansamycin - rifampin | S | S | S |
| Streptogramin- cinu/dalfopristin | S | R | n.a. |
| Oxazolidinone- linezolid | S | S | n.a. |
| Folate inhibitor- trimethoprim | S | R | n.a. |
| Glycopeptide - vancomycin | S | S | S |

|  | *Lactobacillus saliv.* ssp. *Saliv.*, DSM 16351 | *Lactobacillus salivarius*, reference strain 1 | *Lactobacillus salivarius*, reference strain 2 |
|---|---|---|---|
| β-Lactame - ampicillin | S | S | S |
| Amphenicol - chloroamphenicol | S | S | S |
| Tetracyclin | S | S | R |
| Macrolid - erythromycin | S | S | S |
| Ansamycin - rifampin | S | S | S |
| Streptogramin - chinu/dalfopristin | S | R | S |
| Oxazolidinone - linezolid | S | S | S |
| Folate inhibitor - trimethoprim | S | R | R |

|  | *Lactobacillus reuteri*, DSM 16350 | *Lactobacillus reuteri*, reference strain |
|---|---|---|
| Amphenicol - chloramphenicol | S | S |
| Mcrolid - erythromycin | S | R |
| Ansamycin - rifampin | S | S |
| Streptogramin - chinu/dalfopristin | S | R |
| Oxazolidinone - linezolid | S | S |

| | Bifidobacterium animalis, DSM 16284 |
|---|---|
| β-Lactame - ampicillin | S |
| Aminoglycosides | |
| Neomycin | S |
| Gentamicin | S |
| Amphenicol - chloroamphenicol | S |
| Tetraciclin | S |
| Macrolid - erythromycin | S |
| Ansamycin - rifampin | S |
| Strptogramin - chinu/dalfopristin | S |
| Fluorochinolone- enrofloxacin | S |
| Oxazolidinone- linezolid | S |
| Folate inhibitor - trimethoprim | S |
| Glycopeptid- vancomycin | S |

S . . . sensitive,
R . . . resistent

From these comparative tests results that none of the deposited microorganisms became resistant to any of the known antibiotics tested, they all remained sensitive and susceptible.

Annex to PCT application
Applicant: Erber Aktiengesellschaft et al.

List pursuant to Rule 13bis, para 4, of the Regulations Under the Patent Cooperation Treaty.

All of the microorganisms mentioned in the present application were deposited at the German Collection of Microorganisms and Cell Cultures GmbH--DSMZ, Mascheroder Weg 1b, 38124Braunschweig, Germany (DE), the recognized IDA under the Budapest Treaty on the International Recognition of the Deposit of Microorganisms for the Purposes of Patent Procedure on the following dates, and have been given the following access numbers.

| Accession number | Accession date |
|---|---|
| DSM 16284 | Mar. 10, 2004 |
| DSM 16211 | Feb. 06, 2004 |
| DSM 16210 | Feb. 06, 2004 |
| DSM 16350 | Apr. 15, 2004 |
| DSM 16351 | Apr. 15, 2004 |

The invention claimed is:

1. A probiotic health and performance promoting food, feed and/or drinking water additive containing a mixture of biologically pure microorganisms, wherein the mixture comprises at least two biologically pure microorganisms selected from the group consisting of *Enterococcus faecium* DSM 16211, *Lactobacillus reuteri* DSM 16350, *Lactobacillus salivarius* ssp. *salivarius* DSM 16351, *Pediococcus acidilactici* DSM 16210, and *Bifidobacterium animalis* DSM 16284.

2. The additive according to claim 1, wherein the mixture comprises at least three biologically pure microorganisms.

3. The additive according to claim 1, wherein the mixture comprises the biologically pure *Enterococcus faecium* DSM 16211, the biologically pure *Lactobacillus reuteri* DSM 16350, and the biologically pure *Lactobacillus salivarius* ssp. *salivarius* DSM 16351.

4. The additive according to claim 1, wherein the mixture comprises the biologically pure *Enterococcus faecium* DSM 16211, the biologically pure *Pediococcus acidilactici* DSM 16210, and the biologically pure *Bifidobacterium animalis* DSM 16284.

5. The additive according to claim 1, wherein the additive further comprises nutritive substances and/or prebiotic substances selected from the group consisting of fructo-oligosaccharides, inulins, isomalto-oligosaccharides, lactitol, lactosucrose, lactulose, pyrodextrines, soy oligosaccharides, transgalacto-oligosaccharides, xylo-oligosaccharides and vitamins.

6. The additive according to claim 1, wherein the additive further comprises a carrier selected from the group consisting of zeolites, calcium carbonate, magnesium carbonate, trehalose, chitosan, shellac, albumin, starch, skim-milk powder, sweet-whey powder, maltodextrin, lactose, inulin, dextroses and vegetable oils, or a solvent selected from water or physiologic saline solution.

7. The additive according to claim 1, wherein the additive further comprises a coating material selected from the group consisting of maltodextrins, guar seed flour, gum arabic, alginates, starch, dextrins, cellulose gelatine, albumin, casein, gluten, acacia gum, tragacanth, waxes, paraffin, stearic acid and mono- and diglycerides.

8. The additive according to claim 1, wherein the additive further comprises at least one additional microorganism selected from the group consisting of *Bifidobacterium* sp., *Lactobacillus salivarius Lactobacillus* sp., *Lactobacillus fermentum* and *Enterococcus faecalis*.

9. The additive according to claim 1, wherein the biologically pure microorganisms are contained in suspended, powdery or encapsulated form.

10. The additive according to claim 1, wherein said feed additive is comprised of $1\times10^7$ to $1\times10^{14}$ of CFU/kg feed additive of *Enterococcus faecium* DSM 16211, and $1\times10^6$ to $1\times10^{14}$ of CFU/kg feed additive of *Lactobacillus reuteri* DSM 16350.

11. The additive according to claim 1, wherein said feed additive is comprised of $1\times10^7$ to $1\times10^{14}$ of CFU/kg feed additive of *Enterococcus faecium* DSM 16211, $1\times10^7$ to $1\times10^{14}$ of, CFU/kg feed additive of *Pediococcus acidilactici* DSM 16210, and $1\times10^7$ to $1\times10^{14}$ of CFU/kg feed additive of *Bifidobacterium animalis* DSM 16284.

12. The additive according to claim 1, wherein said feed additive is comprised of $1\times10^7$ to $1\times10^{14}$ of CFU/kg feed additive of *Enterococcus faecium* DSM 16211, $1\times10^6$ to $1\times10^{14}$ of CFU/kg feed additive of *Lactobacillus reuteri* DSM 16350,and $1\times10^6$ to $1\times10^{14}$ of CFU/kg feed additive of *Lactobacillus salivarius* ssp. *salivarius* DSM 16351.

13. The additive according to claim 1, wherein said feed additive is comprised of $1\times10^7$ to $1\times10^{14}$ of CFU/kg feed additive of *Enterococcus faecium* DSM 16211, $1\times10^6$ to $1\times10^{14}$ of CFU/kg feed additive of *Lactobacillus reuteri* DSM 16350, $1\times10^6$ to $1\times10^{14}$ of CFU/kg feed additive of *Lactobacillus salivarius* ssp. *salivarius* DSM 16351, $1\times10^7$ to $1\times10^{14}$ of CFU/kg feed additive of *Pediococcus acidilactici* DSM 16210, $1\times10^7$ to $1\times10^{14}$ of CFU/kg feed additive of *Bifidobacterium animalis* DSM 16284, and $1\times10^6$ to $1\times10^{14}$ of CFU/kg, feed additive of *Bifidobacterium* sp.

14. The additive according to claim 11, wherein the feed additive additionally comprises 1% to 95% of a carrier or the additive is an aqueous suspension present in an effective amount of from 0.01 g/kg to 10 g/kg feed.

15. The feed additive according to claim 10, wherein the feed additive is mixed into animal feed in an effective amount of from 20 g/t to 20 kg/t.

16. The additive according to claim 1, wherein the drinking water additive comprises $1\times10^7$ to $1\times10^{14}$ of CFU/kg drinking water additive of *Enterococcus faecium* DSM 16211, and $1\times10^6$ to $1\times10^{14}$ of CFU/kg drinking water additive of *Lactobacillus reuteri* DSM 16350.

17. The additive according to claim 1, wherein the drinking water additive is comprised of $1\times10^7$ to $1\ 10^{14}$ of CFU/kg drinking water additive of *Enterococcus faecium* DSM 16211, $1\times10^6$ to $1\times10^{14}$ of CFU/kg drinking water additive of *Lactobacillus reuteri* DSM 16350, and $1\times10^6$ to $1\times10^{14}$ of CFU/kg drinking water additive of *Lactobacillus salivarius* ssp. *salivarius* DSM 16351.

18. The additive according to claim 1, wherein the drinking water additive is comprised of $1\times10^7$ to $1\times10^{19}$ of CFU/kg drinking water additive of *Enterococcus faecium* DSM 16211, $1\times10^7$ to $1\times10^{14}$ of CFU/kg drinking water additive of *Pediococcus acidilactici* DSM 16210, and $1\times10^7$ to $1\times10^{14}$ of CFU/kg drinking water additive of *Bifidobacterium animalis* DSM 16284.

19. The additive according to claim 1, wherein the drinking water additive is comprised of $1\times10^7$ to $1\times10^{14}$ of CFU/kg drinking water additive of *Enterococcus faecium* DSM 16211, $1\times10^6$ to $1\times10^{14}$ of CFU/kg drinking water additive of *Lactobacillus reuteri* DSM 16350, $1\times10^6$ to $1\times10^{14}$ of CFU/kg drinking water additive of *Lactobacillus salivarius* ssp. *salivarius* DSM 16351, $1\times10^7$ to $1\times10^{14}$ of CFU/kg drinking water additive of *Pediococcus acidilactici* DSM 16210, $1\times10^7$ to $1\times10^{14}$ of CFU/kg drinking water additive of *Bifidobacterium animalis* DSM 16284, and $1\times10^6$ to $1\times10^{14}$ of CFU/kg drinking water additive of *Bifidobacterium* sp.

20. The additive according to claim 16, wherein the drinking water additive additionally comprises 1% to 95% of a carrier or nutrient.

21. A method of manufacturing a probiotic health and performance promoting food, feed and/or drinking water additive, comprising the step of mixing at least two biologically pure microorganisms selected from the group consisting of *Enterococcus faecium* DSM 16211, *Lactobacillus reuteri* DSM 16350, and *Lactobacillus salivarius* ssp. *salivarius* DSM 16351, *Pediococcus acidilactici* DSM 16210, and *Bifidobacterium animalis* DSM 16284 to produce said additive comprising the mixture of microorganisms.

22. The method according to claim 21, wherein *Enterococcus faecium* DSM 16211, *Lactobacillus reuteri* DSM 16350, and *Lactobacillus salivarius* ssp. *salivarius* DSM 16351, are selected or wherein *Enterococcus faecium* DSM 16211, *Pediococcus acidilactici* DSM 16210, and *Bifidobacterium animalis* DSM 16284, are selected or wherein *Enterococcus faecium* DSM 16211and *Lactobacillus reuteri* DSM 16350 are selected and combined with additional microorganisms of *Lactobacilli*, *Streptococci* and/or *Bifidobacteria*.

23. The method according to claim 21, wherein the mixture of microorganisms is further mixed with at least one gelatinizing agent selected from maltodextrins, guar seed flour, gum arabic, alginates, starch, dextrins, cellulose, proteins, acacia gum, tragacanth,and lipids.

24. The method according to claim 21, further comprising adding a liquid carrier to the mixture of microorganisms to form a spray suspension.

25. A method to increase immune defense of an animal subject comprising the step of administering to the subject a mixture of at least two biologically pure microorganisms selected from the group consisting of *Enterococcus faecium* DSM 16211, *Lactobacillus reuteri* DSM 16350, *Lactobacillus salivarius* ssp. *salivarius* DSM 16351,*Pediococcus acidilactici* DSM 16210, and *Bifidobacterium animalis* DSM 16284.

* * * * *

SEQUENCE LISTING

```
<160> NUMBER OF SEQ ID NOS: 5

<210> SEQ ID NO 1
<211> LENGTH: 1094
<212> TYPE: DNA
<213> ORGANISM: Pediococcus acidilactici
<220> FEATURE:
<221> NAME/KEY: 16S-rDNA
<222> LOCATION: (1)..(1094)
<300> PUBLICATION INFORMATION:
<308> DATABASE ACCESSION NUMBER: DSM 16210
<309> DATABASE ENTRY DATE: 2004-02-06
<313> RELEVANT RESIDUES IN SEQ ID NO: (1)..(1094)

<400> SEQUENCE: 1
cctggctcag gatgaacgct ggcggcgtgc ctaatacatg caagtcgaac gaacttccgt      60
taattgatta tgacgtgctt gcactgaatg agattttaac acgaagtgag tggcggacgg     120
gtgagtaaca cgtgggtaac ctgcccagaa gcagggata acacctggaa acagatgcta     180
ataccgtata acagagaaaa ccgcctggtt ttcttttaaa agatggctct gctatcactt     240
ctggatggac ccgcggcgca ttagctagtt ggtgaggtaa cggctcacca aggcgatgat     300
gcgtagccga cctgagaggg taatcggcca cattgggact gagacacggc ccagactcct     360
acgggaggca gcagtaggga atcttccaca atggacgcaa gtctgatggt gcacgccgcg     420
tgagtgaaga agggtttcgg ctcgtaaagc tctgttgtta aagaagaacg tgggtgagag     480
taactgttca cccagtgacg gtatttaacc agaaagccac ggctaactac gtgccagcag     540
ccgcggtaat acgtaggtgg caagcgttat ccggatttat tgggcgtaaa gcgagcgcag     600
gcggtctttt aagtctaatg tgaaagcctt cggctcaacc gaagaagtgc attggaaact     660
gggagacttg agtgcagaag aggatagtgg aactccatgt gtagcggtga aatgcgtaga     720
tatatggaag aacaccagtg gcgaaggcgg ctgtctggtc tgtaactgac gctgaggctc     780
gaaagcatgg gtagcgaaca ggattagata ccctggtagt ccatgccgta aacgatgatt     840
```

```
actaagtgtt ggagggtttc cgcccttcag tgctgcagct aacgcattaa gtaatccgcc    900
tggggagtac gaccgcaagg ttgaaactca aaagaattga cggggcccg cacaagcggt     960 ggagcatgtg gtttaattcg aagctacgcg aagaacctta ccaggtcttg acatcttctg   1020
ccaacctaag agattaggcg ttcccttcgg ggacagaatg acaggtggtg catggttgtc   1080
gtcagctcgt gtcg                                                     1094
```

<210> SEQ ID NO 2
<211> LENGTH: 1083
<212> TYPE: DNA
<213> ORGANISM: Lactobacillus reuteri
<220> FEATURE:
<221> NAME/KEY: 16S-rDNA
<222> LOCATION: (1)..(1083)
<300> PUBLICATION INFORMATION:
<308> DATABASE ACCESSION NUMBER: DSM 16350
<309> DATABASE ENTRY DATE: 2004-04-15
<313> RELEVANT RESIDUES IN SEQ ID NO: (1)..(1083)

<400> SEQUENCE: 2

```
ggatgaacgc cggcggtgtg cctaatacat gcaagtcgta cgcactggcc caactgattg     60
atggtgcttg cacctgattg acgatggatc accagtgagt ggcggacggg tgagtaacac    120
gtaggtaacc tgccccggag cggggggataa catttggaaa cagatgctaa taccgcataa    180
caacaaaagc cacatggctt ttgtttgaaa gatggctttg gctatcactc tgggatggac    240
ctgcggtgca ttagctagtt ggtaaggtaa cggcttacca aggcgatgat gcatagccga    300
gttgagagac tgatcggcca caatggaact gagacacggt ccatactcct acggaggca    360 gcagtaggga atcttccaca atgggcgcaa gcctgatgga gcacaccgcg tgagtgaaga    420
agggtttcgg ctcgtaaagc tctgttgttg gagaagaacg tgcgtgagag taactgttca    480
ygcagtgacg gtatccaacc agaaagtcac ggctaactac gtgccagcag ccgcggtaat    540
acgtaggtgg caagcgttat ccggatttat tgggcgtaaa gcgagcgcag gcggttgctt    600
aggtctgatg tgaaagcctt cggcttaacc gaagaagtgc atcggaaacc gggcgacttg    660
agtgcagaag aggacagtgg aactccatgt gtagcggtgg aatgcgtaga tatatggaag    720
aacaccagtg gcgaaggcgg ctgtctggtc tgcaactgac gctgaggctc gaaagcatgg    780
gtagcgaaca ggattagata ccctggtagt ccatgccgta acgatgagt gctagggtgt     840 tggagggttt ccgcccttca gtgccggagc taacgcatta agcactccgc ctggggagta    900
cgaccgcaag gttgaaactc aaaggaattg acggggcccg cacaagcgg tggaagcatg    960 tggtttaatt cgaagctacg cgaagaacct taccaggtct tgacatcttg cgctaacctt   1020
agagataagg cgttcccttc ggggacgcaa tgacaggtgg tgcatggtcg tcgtcagctc   1080
gtg                                                                  1083
```

<210> SEQ ID NO 3
<211> LENGTH: 1066
<212> TYPE: DNA
<213> ORGANISM: Lactobacillus salivarius ssp. salivarius
<220> FEATURE:
<221> NAME/KEY: 16S-rDNA
<222> LOCATION: (1)..(1066)
<220> FEATURE:
<221> NAME/KEY: misc_feature
<222> LOCATION: (166)..(166)
<223> OTHER INFORMATION: n is a, c, g, t or u
<220> FEATURE:
<221> NAME/KEY: misc_feature
<222> LOCATION: (185)..(185)
<223> OTHER INFORMATION: n is a, c, g, t or u
<220> FEATURE:

```
<221> NAME/KEY: misc_feature
<222> LOCATION: (213)..(213)
<223> OTHER INFORMATION: n is a, c, g, t or u
<220> FEATURE:
<221> NAME/KEY: misc_feature
<222> LOCATION: (236)..(236)
<223> OTHER INFORMATION: n is a, c, g, t or u
<220> FEATURE:
<221> NAME/KEY: misc_feature
<222> LOCATION: (257)..(257)
<223> OTHER INFORMATION: n is a, c, g, t or u
<220> FEATURE:
<221> NAME/KEY: misc_feature
<222> LOCATION: (266)..(266)
<223> OTHER INFORMATION: n is a, c, g, t or u
<220> FEATURE:
<221> NAME/KEY: misc_feature
<222> LOCATION: (292)..(292)
<223> OTHER INFORMATION: n is a, c, g, t or u
<300> PUBLICATION INFORMATION:
<308> DATABASE ACCESSION NUMBER: DSM 16351
<309> DATABASE ENTRY DATE: 2004-04-15
<313> RELEVANT RESIDUES IN SEQ ID NO: (1)..(1066)

<400> SEQUENCE: 3
acgctggcgg cgtgcctaat acatgcaagt cgaacgaaac tttcttacac cgaatgcttg      60
cattcactcg taagaagttg agtggcggac gggtgagtaa cacgtgggta acctgcctaa     120
aagaagggga taacacttgg aaacaggtgc taataccgta tatctntaag gatcgcatga     180
tcctnagatg aaagatggtt ctgctatcgc ttntagatgg acccgcggcg tattanctag     240
ttggtggggt aacggcntac caaggngatg atacgtagcc gaactgagag gntgatcggc     300
cacattggga ctgagacacg gcccaaactc ctacgggagg cagcagtagg gaatcttcca     360
caatggacgc aagtctgatg gtgcccgccg cgagagtgaa gaaggtcttc ggatcgtaaa     420
actctgttgt tagagaagaa cacgagtgag agtaactgtt cattcgatga cggtatctaa     480
ccagcaagtc acggctaact acgtgccagc agccgcggta atacgtaggt ggcaagcgtt     540
gtccggattt attgggcgta aagggaacgc aggcggtctt ttaagtctga tgtgaaagcc     600
ttcggcttaa ccggagtagt gcattggaaa ctggaagact tgagtgcaga agaggagagt     660
ggaactccat gtgtagcggt gaaatgcgta gatatatgga agaacaccag tggcgaaagc     720
ggctctctgg tctgtaactg acgctgaggt tcgaaagcgt gggtagcaaa caggattaga     780
taccctggta gtccacgccg taaacgatga atgctaggtg ttggagggtt tccgcccttc     840
agtgccgcag ctaacgcaat aagcattccg cctggggagt acgaccgcaa ggttgaaact     900
caaaggaatt gacgggggcc cgcacaagcg gtggagcatg tggtttaatt cgaagcaacg     960
cgaagaacct taccaggtct tgacatcctt tgaccaccta aaaaattagg tttcccttcg    1020
gggacaaagt gacaggtggt gcatggctgt cgtcagctcg tgtcgt               1066

<210> SEQ ID NO 4
<211> LENGTH: 1033
<212> TYPE: DNA
<213> ORGANISM: Enterococcus faecium
<220> FEATURE:
<221> NAME/KEY: 16S-rDNA
<222> LOCATION: (1)..(1033)
<300> PUBLICATION INFORMATION:
<308> DATABASE ACCESSION NUMBER: DSM 16211
<309> DATABASE ENTRY DATE: 2004-02-06
<313> RELEVANT RESIDUES IN SEQ ID NO: (1)..(1033)

<400> SEQUENCE: 4
cctggctcag gacgaacgct ggcggcgtgc ctaatacatg caagtcgaac gcttcttttt      60
ccaccggagc ttgctccacc ggaaaaagag gagtggcgaa cgggtgagta acacgtgggt     120
```

```
aacctgccca tcagaagggg ataacacttg gaaacaggtg ctaataccgt ataacaatca      180
aaaccgcatg gttttgattt gaaaggcgct ttcgggtgtc gctgatggat ggacccgcgg      240
tgcattagct agttggtgag gtaacggctc accaaggcca cgatgcatag ccgacctgag      300
agggtgatcg gccacattgg gactgagaca cggcccaaac tcctacggga ggcagcagta      360
gggaatcttc ggcaatggac gaaagtctga ccgagcaacg ccgcgtgagt gaagaaggtt      420
ttcggatcgt aaaactctgt tgttagagaa gaacaaggat gagagtaact gttcatccct      480
tgacggtatc taaccagaaa gccacggcta actacgtgcc agcagccgcg gtaatacgta      540
ggtggcaagc gttgtccgga tttattgggc gtaaagcgag cgcaggcggt ttcttaagtc      600
tgatgtgaaa gccccccggct caaccgggga gggtcattgg aaactgggag acttgagtgc      660
agaagaggag agtggaattc catgtgtagc ggtgaaatgc gtagatatat ggaggaacac      720
cagtggcgaa ggcggctctc tggtctgtaa ctgacgctga ggctcgaaag cgtggggagc      780
aaacaggatt agataccctg gtagtccacg ccgtaaacga tgagtgctaa gtgttggagg      840
gtttccgccc ttcagtgctg cagctaacgc attaagcact ccgcctgggg agtacgaccg      900
caaggttgaa actcaaagga attgacgggg cccgcacaa gcggtggagc atgtggttta      960
attcgaagca acgcgaagaa ccttaccagg tcttgacatc ctttgaccac tctagagata     1020
gagcttcccc ttc                                                       1033

<210> SEQ ID NO 5
<211> LENGTH: 1139
<212> TYPE: DNA
<213> ORGANISM: Bifidocacterium animalis
<220> FEATURE:
<221> NAME/KEY: 16S-rDNA
<222> LOCATION: (1)..(1139)
<220> FEATURE:
<221> NAME/KEY: misc_feature
<222> LOCATION: (286)..(286)
<223> OTHER INFORMATION: n is a, c, g, t or u
<220> FEATURE:
<221> NAME/KEY: misc_feature
<222> LOCATION: (316)..(316)
<223> OTHER INFORMATION: n is a, c, g, t or u
<220> FEATURE:
<221> NAME/KEY: misc_feature
<222> LOCATION: (328)..(328)
<223> OTHER INFORMATION: n is a, c, g, t or u
<220> FEATURE:
<221> NAME/KEY: misc_feature
<222> LOCATION: (351)..(352)
<223> OTHER INFORMATION: n is a, c, g, t or u
<220> FEATURE:
<221> NAME/KEY: misc_feature
<222> LOCATION: (355)..(355)
<223> OTHER INFORMATION: n is a, c, g, t or u
<220> FEATURE:
<221> NAME/KEY: misc_feature
<222> LOCATION: (357)..(357)
<223> OTHER INFORMATION: n is a, c, g, t or u
<220> FEATURE:
<221> NAME/KEY: misc_feature
<222> LOCATION: (389)..(390)
<223> OTHER INFORMATION: n is a, c, g, t or u
<220> FEATURE:
<221> NAME/KEY: misc_feature
<222> LOCATION: (409)..(409)
<223> OTHER INFORMATION: n is a, c, g, t or u
<220> FEATURE:
<221> NAME/KEY: misc_feature
<222> LOCATION: (411)..(411)
<223> OTHER INFORMATION: n is a, c, g, t or u
<220> FEATURE:
<221> NAME/KEY: misc_feature
<222> LOCATION: (413)..(413)
```

<223> OTHER INFORMATION: n is a, c, g, t or u
<220> FEATURE:
<221> NAME/KEY: misc_feature
<222> LOCATION: (418)..(418)
<223> OTHER INFORMATION: n is a, c, g, t or u
<300> PUBLICATION INFORMATION:
<308> DATABASE ACCESSION NUMBER: DSM16284
<309> DATABASE ENTRY DATE: 2004-03-10
<313> RELEVANT RESIDUES IN SEQ ID NO: (1)..(1139)

<400> SEQUENCE: 5

```
ttgccatggg cgcaagcctg atgcagcgac gccgcgtgcg ggatggaggc cttcgggttg      60
taaaccgctt ttgttcaagg gcaaggcacg gtttcgggcc gtgttgagtg gattgttcga     120
ataagcaccg gctaactacg tgccagcagc cgcggtaata cgtagggtgc gagcgttatc     180
cggatttatt gggcgtaaag ggctcgtagg cggttcgtcg cgtccggtgt gaaagtccat     240
cgcctaacgg tggatctgcg ccgggtacgg gcgggctgga gtgcgntaag ggagactgga     300
attcccggtg taacgntgga atgtgtanat atcgggaaga acaccaatgg nnaangnagg     360
tctctgggcc gttactgacg ctgacgatnn aaagacgtga accagcganc ncnataanat     420
accctgacta cggattagat accctggtag tccacgccgt aaacggtgga tgctggatgt     480
ggggcccttt ccacgggtcc tgtgtcggag ccaacgcgtt aagcatcccg cctggggagt     540
acggccgcaa ggctaaaact caaagaaatt gacgggggcc cgcacaagcg gcggagcatg     600
cggattaatt cgatgcaacg cgaagaacct tacctgggct tgacatgtgc cggatcgccg     660
tggaaacacg gtttccttc ggggccggtt cacaggtggt gcatggtcgt cgtcagctcg     720
tgtcgtgaga tgttgggtta agtcccgcaa cgagcgcaac cctcgccgca tgttgccagc     780
gggtgatgcc gggaactcat gtgggaccgc cggggtcaac tcggaggaag gtggggatga     840
cgtcagatca tcatgcccct tacgtccagg gcttcacgca tgctacaatg gccggtacaa     900
cgcgatgcga cacggtgacg tggggcggat cgctgaaaac cggtctcagt tcggatcgca     960
gtctgcaact cgactgcgtg aaggcggagt cgctagtaat cgcggatcag caacgccgcg    1020
gtgaatgcgt tcccgggcct tgtacacacc gcccgtcaag tcatgaaagt gggtagcacc    1080
ggaagccggt ggcccgaccc tcgtggggcg gaccgtctaa tggtgagact cgtgattgg     1139
```